United States Patent [19]

Bradaczek et al.

[11] Patent Number: 5,047,573

[45] Date of Patent: Sep. 10, 1991

[54] PROCESS FOR THE PRODUCTION OF PEPTIDES USING DIACYLAMINES

[76] Inventors: Hans Bradaczek, Bergengruenstrasse 47, D-100 Berlin 38, Fed. Rep. of Germany; Wojciech Gruszecki; Maria Gruszecki, both of Berlepschstrasse 132, D-100 Berlin 37, Fed. Rep. of Germany

[21] Appl. No.: 123,157

[22] PCT Filed: Feb. 27, 1987

[86] PCT No.: PCT/DE87/00088

§ 371 Date: Dec. 7, 1987

§ 102(e) Date: Dec. 7, 1987

[87] PCT Pub. No.: WO87/05292

PCT Pub. Date: Sep. 11, 1987

[30] Foreign Application Priority Data

Mar. 7, 1986 [DE] Fed. Rep. of Germany ....... 3608083

[51] Int. Cl.$^5$ ................. C07C 205/00; C07C 261/00; C07K 1/00

[52] U.S. Cl. ......................................... 560/21; 560/27; 564/138; 564/139; 564/155; 530/333; 530/334; 530/338

[58] Field of Search ....................... 530/333, 338, 334; 564/138, 139, 155; 560/21, 27

[56] References Cited

PUBLICATIONS

Stedman, T. L., Stedman's Medical Dictionary; 24th Ed., Williams & Wilkins, 1982, p. 1224.
Gruszechi, W. et al., Liebigs Am. Chem.; 4, 331–336, 1988.
Schwarz, P., J. of Org. Chem.; 37(18), 2906–2909, 1972.
Rabson et al., Introduction To Proteins and Protein Engineering, Elsevier Science Publishers; pp. 13–14, 1988.
Stenesh, Dictionary of Biochemistry, Wiley & Sons Publication; pp. 220, 1975.
Vlassa, M. et al.; Revue Roumaine de Chimie, 22(7): 1111–1114, 1977.
Russell, P. et al.; J Chem. Soc. B(4); pp. 657–661; 1971.
The Journal of Biological Chem., 260, 22, (1985); Section 3AA–9.2, Amides, Anilides and Analogous Derivatives.
Kodak Laboratory and Research Roducts, Catalog No. 53, International Edition; 1987, Catalog & Price List.
A German–English Dictionary For Chemists; Third Edition, Austin M. Patterson.
Dictionary of Chemistry and Chemical Engineering, vol. I German/English; 2nd revised and enlarged edition; L. DeVries, H. Kolb.

Primary Examiner—Howard E. Schain
Assistant Examiner—Susan M. Perkins
Attorney, Agent, or Firm—Cushman, Darby & Cushman

[57] ABSTRACT

Process for the production of peptides of general formula $R^1CO-NHR^2$(1), where $R^1CO$- is the carboxy component and $R^2NH$- is the amino component of a peptide building block. The process is characterized in that a carboxylic acid of general formula $R^1COOH$ (II), where $R^1CO$- has the above meaning, is made to react with a carboxylic acid imide choloride of general formula (III), wherein X is a hydrogen atom, an alkyl group with a maximum of 4 carbon atoms, a fluorine atom, a cholorine atom or a nitro group, Y is a fluorine atom, a chlorine atom or a nitro group and Z has the same meaning as Y or is a hydrogen atom, and the diacylamine of general formula (IV), where $R^1$, C, Y and Z have the above meaning, is bound to an amine of general formula $R^2NH^2$(V), where $R^2NH$- have the above-mentioned meaning.

4 Claims, No Drawings

PROCESS FOR THE PRODUCTION OF PEPTIDES USING DIACYLAMINES

It is well known, that certain diacylamines-containing peptide elements-are suitable for peptide synthesis. For example the N-(N'-phthalyl-glycyl)-N-diphenylacetyl-4-methylaniline has been used for the synthesis of N-Phthalylglycyl-glycyl-glycin-ethyl ether (J. Am. Chem. Soc., 80, 1958, 4069).

To use the claimed diacylamines of formula IV has the advantage of reducing significantly the production expenses of synthesizing peptides. Furthermore in a reaction with amino-components of the formula V the claimed diacylamines give surprising high yield and a high purity of the peptides of formula I. It is surprising for experts, that using the claimed diacylamines of the general formula IV, peptides can be obtained, because these compounds if they contain unsubtituted phenyl grops (i.e. compounds of the general form IV with Y and Z as hydrogen atoms) were found unsuitable for peptide synthesis according to the literature (Biochemistry, 5, 1966, 2468) and the present inventors own experiments.

According to the claimed procedure for production of peptides of the general formula I,

  (I)

in which
$R_1CO$—denotes the carboxyl-component of an N-protected amino acid or peptide and
$R_2NH$—denotes an amino-component of an amino acid or peptide ester or salt,
where the amino acid or peptide residues enclosed in $R_1$ and $R_2$ are the same or different, a carboxyl acid of the general formula II

  (II)

in which $R_1CO$—has the above mentioned meaning is reacted with carboxylic-acid-imidoylchloride of the general formula III,

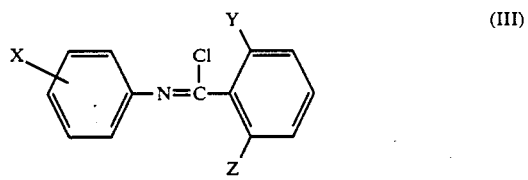  (III)

in which
X—denotes a hydrogen or halogen atom, a nitro— or an alkyl-group with maximal 4-C atoms,
Y—denotes a halogen atom or nitro group and
Z—has the same meaning as Y or denotes a hydrogen atom,
and the resulting diacylamine of the general formula IV

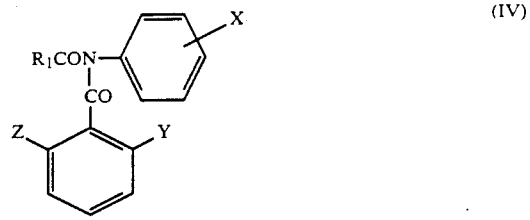  (IV)

in which
$R_1CO$, X, Y and Z denote the above mentioned meaning,
is coupled with an amine of the general formula V

  (V)

in which $R_2NH$—denotes the above mentioned meaning.

According to the claimed procedure, in the first reaction step a carboxylic acid of the general formula II reacts with a imidoylchloride of the general formula III. This reaction can be done preferably in a inert solvent containing bases. Suitable solvents are, for example, lower alcohols such as methanol, ethanol or isopropanol, lower carboxylic acid ester, such as ethyl acetate, polar ether such as dioxan, tetrahydrofuran, glycol monoethylether or dimethylether (diglyme), ketones such as acetone, methylacetone or methylisobutylketone and dipolar aprotic solvents, such as dimethylformamide, N-methylacetamide, tetramethylene sulfone (sulfolan) or hexamethylphosphoramide. Furthermore, suitable solvents include mixtures of the above mentioned with inert and nonpolar solvents such as chloronated hydrocarbons (dichloromethane, trichloromethane or tetrachloroethane etc.) or aromatic hydrocarbons (benzene, toluene etc.). Suitable bases are for example tertiary amines such as triethylamine, tributylamine, N-methylmorpholine or N-ethylpiperazine, inorganic bases such as caustic soda solution or potash, alkali metals carbonate such as natron sodium bicarbonate, potassium carbonate or potassium bicarbonate and alkali metals alcoholates such as natriummethylate or potassium ethylate. Usually this first reaction step is carried out under a temperature of $-20°$ C. to $100°$ C., where a temperature between $0°$ C. to $30°$ C. is preferred for economical reasons. Diacylamines of the general formula IV

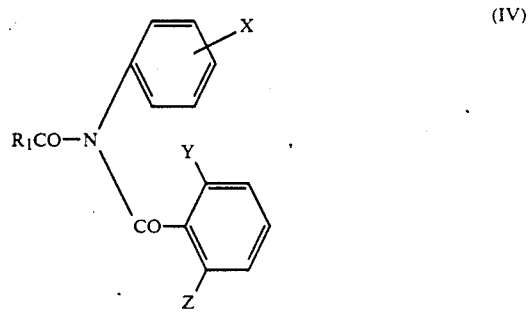  (IV)

in which
$R_1CO$—denotes the acylating carboxy-component used in peptide synthesis; X denotes a hydrogen atom, a halogen atom, an acyl with 4C-atoms or a nitrogroup;
Y denotes a halogen atom or nitrogroup; and Z has the same meaning as Y or denotes a hydrogen atom, are obtained. Examples of such diacylamines include
N-(2-nitrobenzoyl)-N-(N'-tert-butyloxycarbonyl-glycyl)-aniline, N-(2-chlorobenzoyl)-N-(N'-tert-butyloxycarbonyl-L-alanyl)-aniline and
N-(2,6-dichlorbenzoyl)-N-(N'-tert-butyloxycarbonyl-L-phenylalanyl) alanine;

In the second step of the claimed procedure, the diacylamine of formula IV obtained in the first step reacts with an amine of the general formula V. This reaction step is performed preferably in an inert solvent. The same solvents as in the first reaction step can be used. The temperature of the reaction is in the range from −20° C. to 100° C., where −10° C. to 30° C. is preferred.

The claimed procedure is useable for universal peptide synthesis like established procedures (Houben-Weyl "Methoden der organischen Chemie", Georg Thieme Verlag, Stuttgart BR-Deutschland, Band XV/1 "Synthese von Peptiden" Teil I, 1974 und Band XV/2 "Synthese von Peptiden" Teil II, 1974). As in the established procedures, in the claimed procedure it is useful to protect in known ways other amino groups-as well as if necessary-present hydroxygroups, thiogroups and other carboxylgroups of the substrates of carboxylic acids not used. Carboxylic acids of the general formula II, suitable for the claimed procedure are for instance N-protected peptide chains of the general formula IIa

$$V\text{-}(Am_1\text{-}Am_2 \ldots Am_x)OH \qquad (IIa),$$

in which $Am_1$, $Am_2 \ldots Am_x$ represent natural or synthetic amino acid residues being coupled in a peptide chain of up to 16 residues, and V represents an amino-protecting group, such as for example, the benzyloxycarbonyl group or the tert.-butoxy carbonyl group.

As a fragment $Am_1$, $Am_2 \ldots Am_z$ can be mentioned aminoacids for example HoppeSeyler's Z. Physiol. Chem. 348, 1967, 256-261) in the case that possible existing hydroxyl-, thiol-, amino- and for the reaction not used other carboxylgroups are protected.

The hydroxyl-, thio-, carboxyl- and other reacting amino groups of the amines of the general formula V which are not used are protected in well known ways.

Suitable amines are for instance peptide-derivates of the general formula Va

$$H(Am_1\text{-}Am_2 \ldots Am_x)\text{-}OW \qquad (V\ a),$$

in which the $Am_1$, $Am_2 \ldots Am_x$ have the above mentioned meaning and OW represents a carboxylacid protection group, for example, lower alcoxygroups with maximal 4 C-atoms, such as the methoxy-, ethoxy- or the tert.-butyloxygroup or a benzyloxygroup or W is an alkalimetal atom such as sodium or potassium respectively a trialkylammonium-cation with maximal 4 C-atoms per alkylgroup.

To carry out the claimed procedure carboxylimidoylchlorides of the general formula III are necessary carboxylimidoylchlorides can be produced from special substituted N-benzoylanilines by reaction with chlorination agents such as phosphorpentachloride or thionylchloride.

In a typical procedure in the first step of the present peptide production process the diacylamine is prepared. For example, 10 mmol of a Boc-amino acid dissolved in 50 ml of ethyl acetate or toluene reacts for 4 hours with 10 mmol of N-phenyl-N-(2,6-di-chlorobenzimido)-chloride.

The product is then washed with a small amount of water, dryed with $NaSO_4$ and the organic solvent is evaporated. The resulting solid product, often in foam-form, is ready to be used in the next step of the process. The diacylamines usually can be obtained with a high yield in crystalline form and can be retained for an extended period without decomposition.

In the next step of the process of peptide production, the obtained diacylamines containing Boc- or different protected amino acid fragment, react with an amino group of the amino acids or peptides. Thus, for example, the above diacylamines in an equivalent amount or in excess react with a free peptide in a lower alcohol solvent and in the presence of an equivalent of triethylamine or other bases.

The product N-protected peptide chain of up to 16 residues, can be easily separated from the other neutral components and by products (excess of the diacylamine, relevant anilide etc.) by one of the methods well known in peptide chemistry. One of the main advantages of the claimed process is its great selectivity in the reaction which results in pure and easily separated products.

The following examples explain the claimed procedure.

I. SYNTHESIS OF CARBOXYLIC-ACID-IMIDOYLCHLORIDES

EXAMPLE 1

12.0 g of N-(2-nitrobenzoyl)-aniline and 10.0 g phosphorpentachloride are mixed in a round bottom flask with a reflex condensor and warmed carefully under exclusion of humidity. Both substances are dissolved with heavy HCL-evaporation. The solution is warmed to boiling and kept boiling for 1 h. Thereafter the phosphoroxychloride is distilted off and the remaining brown oil residue is evaporated two times with 10 ml of absolute the toluene. Then the rest of toluene is removed under a pressure of $10^{-2}$ Torr and a temperature of 80° C. The yield is 12.8 g of the N-phenyl-N-(2-nitrobenzimidoyl)chloride as a brown syrup. (Lit.: R. A. Abramovitsch et al., J. Org. Chem. 48, 4391 (1983)).

EXAMPLE 2

22.0 g of N-(2-chlorobenzoyl)-aniline are mixed with 20.0 g phosphorpentachloride and warmed as in example 1. After heavy HCl evolution the phosphoroxychloride is distilled off, and the oily benzimidoylchloride is purified by distillation under the pressure of $10^{-2}$ Torr (boiling-point about 140° C.). The remaining transparent oil of N-phenyl-N-(2-chlorobenzimidoyl) chloride crystallizes in the receiving flasks and melts at 54° C. (Lit.: A. W. Chapman, J. Chem. Soc., 2296 (1926)).

EXAMPLE 3

23.0 g of N-(2,6-dichlorobenzoyl)-aniline preferably from 2.6-dichlorobenzoylchloride and aniline, m.p. 176°-177° C.) and 18.0 g of phosphorpentachloride are reacted acccording to example 2. The oily product is distilled under the pressure of $10^{-2}$ Torr and at 135° C. One gets 21.0 g crystalline N-phenyl-N-(2,6-dichlorobenzimidoyl)-chloride; m.p. about 35° C.

EXAMPLE 4

15.0 g of N-(2,6-dichlorobenzoyl)-aniline are boiled in 20 ml thionylchloride for 4 hours, then the excess chlorination-agent is distilled off and the resulting oily product is worked up as in example 3. The yield is 15.0 g N-phenyl-N-(2,6-dichlorobenzimidoyl)chloride.

II. PREPARATION OF DIACYLAMINES

EXAMPLE 5

1 mmol (175 mg) of tert-butyloxycarbonylglycine (Boc-GlyOH) is dissolved in 2 ml methanol and neutralized with 1 mM triethylamine (0.14 ml). The solution is cooled down to 0° C. Then 1.1 mM (286.5 mg) N-phenyl-N-(2-nitrobenzimidoyl)chloride in 1 ml toluene (prepared according to example 1) is added and the mixture is stirred at room temperature for 1 h. The solvents are evaporated under low pressure, the residue is dissolved in ethyl acetate and step by step washed with 0.5 n HCl, water, saturated $NaHCO_3$-solution and again with water; then dried with $MgSO_4$ and evaporated in vacuum. Yield: 409.0 mg N-(2-nitrobenzoyl)-N-(N'-tert-butyloxycarbonyl-glycin)anilide as a yellow foam.

EXAMPLE 6

1 mmol (189 mg) of tert-butyloxycarbonyl-L-alanine (Boc-L-Ala-OH) is dissolved in 2 ml ethyl acetate and 0.14 ml triethylamine. After cooling in an ice-bath 255 mg N-phenyl-N-(2-chlorobenzimidoyl)chloride are added and the mixture stirred at room temperature for 30 minutes. Thereafter the solution is washed with 0.5 n HCl, water, $NaHCO_3$-solution and again with water, dried with $MgSO_4$ and evaporated under low pressure. The yield is 400 mg N-(2-chlorobenzoyl)-N-(N'-tert-butyloxycarbonyl-L-alanin-anilide as a white foam.

EXAMPLE 7

1 mmol (265 mg) of N-tert-butyloxycarbonyl-L-phenylalanine (Boc-L-PheOH) is dissolved in 5 ml ethyl acetate and neutralized with 1 n KOH. At 4° C. 1 mM (284 mg) of N-phenyl-N-2,6-dichlorobenzimidoyl)chloride is added and stirred at room temperature for 4 hours; then the water layer is separated. The organic phase is washed first with $NaHCO_3$-solution and then with water, dried with $Na_2SO_4$ and concentrated in vacuum. The oily substance is crystallized in isopropanol. Yield: 413 mg N-(2,6-dichlorobenzoyl)-N-(N'-tert-butyloxycarbonyl-L-phenylalanin)-anilide. M.p. 154° C.

EXAMPLE 8

1 mM (=175 mg) of N-tert-butyloxycarbonylglycine is dissolved in 2 ml acetone and neutralized with 0.14 ml triethylamine. The solution is cooled in an ice bath. Then 290 mg of N-phenyl-N-(2,6-)-chloride is added and the cooling bath is removed. After 3 hours the acetone solution is concentrated in vacuum to a solid and the neutral product is extracted as in example 5. The product is crystallized from toluene. Yield: 410 mg of N-(2,6-dichlorobenzoyl)-N-(N'-tert-butyloxycarbonyl glycin)-anilide with a m.p. of 109°–111° C.

III. SYNTHESIS OF PEPTIDES

EXAMPLE 9

To the solution of 1 mmol (399 mg) of N-(2-nitrobenzoyl)-N-(Boc-glycin)-anilide, prepared according to example 5), in 5 ml acetone and cooled down to 4° C., 1 mmol. (155 mg) glycine ethyl esterhydrochloride and 0.14 ml triethylamine are added. Then the solution is stirred at room temperature for 1 h. The acetone is evaporated at low pressure. The oily mixture is treated with 5 ml of benzene. The occuring crystals (2 nitrobenzanilide) are separated and the solution of benzene is concentrated to a thick oil. Yield: 270 mg oily Boc-Gly-Gly-OEt; the substance contains about 15-20 mg 2-nitrobenzanilide.

A pure dipeptide-ester can be obtained as follow:

a) The raw product is dissolved in ether and obtained crystals are filtrated, then the ether is evaporated and the substance crystallized from benzene/petrolether. Yield: 215 mg crystals. M.p. 60° C.

b) The product is purified by column chromatography on silica gel. (Solvent: benzene or benzene:acetone (6:1). Yield: 255 mg pure Boc-dipeptide-ester.

c) The raw product is dissolved in 2 ml acetone, 1 ml in NaOH is added and stirred at 20 C. for 1 hour. Then acetone is evaporated and the water-solution is washed with ethyl acetate, the hydrolyzate in water is covered with ethyl acetate and acidified with 3 n citric acid (pH=3). The organic layer is dried with $MgSO_4$ and evaporated in vacuum. Yield: 198 mg Boc-Gly-Gly-OH. The melting point is 125°–127° C., crystals are grown from acetone.

d) The raw product is dissolved in 2 ml 1 n HCl in acetic acid and kept at 20° C. for 45 minutes. Then the solvent is evaporated in vacuum and the residue is crystallized from ethanol-ether. Yield: 178 mg H-Gly-Gly-OEt.HCl.

EXAMPLE 10

To a solution of 1 mmol (175 mg) Boc-Gly-OH in 5 ml ethyl acetate, cooled down to 4° C., 0.14 ml triethylamine and 255 mg of N-phenyl-N-(2-chlorobenzimidoyl)chloride—mentioned in example 2—are added. After stirring of the solution at room temperature for 4 hours, it are cooled down again. 1 mmol (363 mg) H-Phe-Phe-OMe.HCl and then 0.14 ml triethylamine is added. (Lit.: K. Eisele et al., Z. Phys. Chem. 356, 848 (1975)). The mixture is stirred at room temperature for 4 hours, then the obtained solid triethylamine-hydrochloride is extracted using a small amount of water, the ester layer is dried with $NaSO_4$ and evaporated in vacuum. The Boc-Gly-Phe-Phe-OMe is separated from 2-chlorobenzanilide using the above mentioned method (example 9a–9d). By the method of example 9a–9d 410–430 mg pure product, melting point by 153°–155° C. is received.

EXAMPLE 11

1 mmol (165 mg) of L-phenylalanine is dissolved in 1 n KOH in methanol and cooled down to −20° C. Then 550 mg (1,3 mmol) of the N-(N'-Boc-Gly)-N-(2,6-dichlorobenzoyl)-aniline, described in example 8, is added and stirred for 1 hour. In addition the reaction mixture is stirred for 2 hours at 0° C., then at room temperature for 1 hour. After this time the methanol is evaporated in vacuum, the residue is dissolved in ethyl acetate and water. The water layer is separated, covered with 5 ml of ethyl acetate and acidified with 3 n citric acid to pH 3. The ester layer is separated and dried with $MgSO_4$, then evaporated to a white foam. After crystallization from acetone, 202 mg of Boc-Gly-L-Phe-OH is obtained, which decomposed at 135° C.

I claim:

1. Diacylamines of the general formula IV

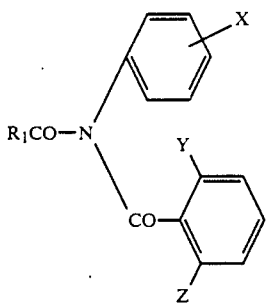

(IV)

in which $R_1CO-$ denotes the carboxy-component of a N-protected amino acid or peptide; X denotes a hydrogen atom, a halogen atom, an acyl with 4C-atoms or a nitro-group;

Y denotes a halogen atom or nitrogroup; and

Z has the same meaning as Y or denotes a hydrogen atom.

2. N-(2-nitrobenzoyl)-N-(N'-tert.-butyloxycarbonyl-glycyl)-anilide.

3. N-(2-chlorbenzoyl)-N-(N'tert.-butyloxycarbonyl-L-alanin anilide.

4. N-(2,6-dichlorbenzoyl)-N-(N'-tert.-butyloxycarbonyl-L-phenylalanin)-anilide.

* * * * *